(12) United States Patent
Aghassian et al.

(10) Patent No.: US 9,227,075 B2
(45) Date of Patent: Jan. 5, 2016

(54) EXTERNAL CHARGER WITH ADJUSTABLE ALIGNMENT INDICATOR

(75) Inventors: Daniel Aghassian, Glendale, CA (US); Lev Freidin, Simi Valley, CA (US); Joey Chen, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1250 days.

(21) Appl. No.: 12/618,637

(22) Filed: Nov. 13, 2009

(65) Prior Publication Data

US 2010/0137948 A1 Jun. 3, 2010

Related U.S. Application Data

(60) Provisional application No. 61/119,671, filed on Dec. 3, 2008.

(51) Int. Cl.
| | |
|---|---|
| *A61N 1/378* | (2006.01) |
| *A61N 1/372* | (2006.01) |
| *H02J 7/02* | (2006.01) |

(52) U.S. Cl.
CPC .......... *A61N 1/3787* (2013.01); *A61N 1/37235* (2013.01); *A61N 1/37252* (2013.01); *A61N 1/37258* (2013.01); *A61N 1/37276* (2013.01); *H02J 7/025* (2013.01)

(58) Field of Classification Search
CPC ............ A61N 1/3787; A61N 1/36125; A61N 1/37229; A61N 1/37223; A61N 1/37217; A61N 1/08; A61N 1/37235; A61N 1/378; A61N 1/025; A61N 1/37211; A61N 1/37252; A61N 1/37276; A61N 1/37258; A61B 5/0031

USPC .......................................... 607/60, 61, 46, 33
See application file for complete search history.

(56) References Cited

U.S. PATENT DOCUMENTS

| | | | |
|---|---|---|---|
| 3,646,940 A | 3/1972 | Timm et al. | |
| 3,822,708 A | 7/1974 | Zilber | |
| 5,690,693 A * | 11/1997 | Wang et al. ..................... | 607/61 |
| 6,516,227 B1 | 2/2003 | Meadows et al. | |
| 2004/0039423 A1* | 2/2004 | Dolgin ........................... | 607/27 |
| 2005/0075693 A1* | 4/2005 | Toy et al. ........................ | 607/60 |
| 2005/0119716 A1* | 6/2005 | McClure et al. ................ | 607/61 |
| 2006/0161225 A1* | 7/2006 | Sormann et al. ................ | 607/61 |
| 2008/0288025 A1* | 11/2008 | Peterson ......................... | 607/60 |
| 2009/0112291 A1* | 4/2009 | Wahlstrand et al. ............ | 607/61 |

* cited by examiner

*Primary Examiner* — Christopher D Koharski
*Assistant Examiner* — Jeremiah Kimball
(74) *Attorney, Agent, or Firm* — Lewis & Reese, PLLC

(57) ABSTRACT

Electrical energy is transcutaneously transmitted at a plurality of different frequencies to an implanted medical device. The magnitude of the transmitted electrical energy respectively measured at the plurality of frequencies. One of the frequencies is selected based on the measured magnitude of the electrical energy (e.g., the frequency at which the measured magnitude of the electrical energy is the greatest). A depth level at which the medical device is implanted within the patient is determined based on the selected frequency. For example, the depth level may be determined to be relatively shallow if the selected frequency is relatively high, and relatively deep if the selected frequency is relative low. A charge strength threshold at which a charge strength indicator generates a user-discernible signal can then be set based on the determined depth level.

33 Claims, 6 Drawing Sheets

| FREQUENCY (KHz) | DEPTH (mm) |
|---|---|
| 177 | 0 |
| 77.1 | 0.125 |
| 77.2 | 0.250 |
| 77.3 | 0.375 |
| 77.4 | 0.500 |

| 114.3 | 49.125 |
|---|---|
| 114.4 | 49.250 |
| 114.5 | 49.375 |
| 114.6 | 49.500 |
| 114.7 | 49.625 |
| 114.8 | 49.750 |
| 114.9 | 49.875 |
| 115 | 50.000 |

EXTERNAL CHARGER WITH ADJUSTABLE ALIGNMENT INDICATOR

RELATED APPLICATION

The present application claims the benefit under 35 U.S.C. §119 to U.S. provisional patent application Ser. No. 61/119,671, filed Dec. 3, 2008. The foregoing application is hereby incorporated by reference into the present application in its entirety.

FIELD OF THE INVENTION

The present invention relates to implantable devices, and more particularly, to devices for transcutaneously recharging devices implanted within patients.

BACKGROUND OF THE INVENTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a spinal cord stimulation system, such as that disclosed in U.S. Pat. No. 6,516,227 ("the '227 patent"), issued Feb. 4, 2003 in the name of inventors Paul Meadows et al., which is incorporated herein by reference in its entirety.

Spinal cord stimulation is a well-accepted clinical method for reducing pain in certain populations of patients. A spinal cord stimulation (SCS) system typically includes an implantable pulse generator and at least stimulation electrode lead that carries electrodes that are arranged in a desired pattern and spacing to create an electrode array. Individual wires within the electrode lead(s) connect with each electrode in the array. The electrode lead(s) is typically implanted along the dura of the spinal cord, with the electrode lead(s) exiting the spinal column, where it can generally be coupled to one or more electrode lead extensions. The electrode lead extension(s), in turn, are typically tunneled around the torso of the patient to a subcutaneous pocket where the implantable pulse generator is implanted. Alternatively, the electrode(s) lead may be directly coupled to the implantable pulse generator. For examples of other SCS systems and other stimulation systems, see U.S. Pat. Nos. 3,646,940 and 3,822,708, which are hereby incorporated by reference in their entireties.

Of course, implantable pulse generators are active devices requiring energy for operation. Oftentimes, it is desirable to recharge an implanted pulse generator via an external charger, so that a surgical procedure to replace a power depleted implantable pulse generator can be avoided. To wirelessly convey energy between the external charger and the implanted pulse generator, the recharger typically includes an alternating current (AC) charging coil that supplies energy to a similar charging coil located in or on the implantable pulse generator. This system is like a loosely coupled inductive transformer where the primary coil is in the external charger and the secondary coil is in the implanted pulse generator. The energy received by the charging coil located on the implantable pulse generator can then be used to directly power the electronic componentry contained within the pulse generator, or can be stored in a rechargeable battery within the pulse generator, which can then be used to power the electronic componentry on-demand.

To provide efficient power transmission through tissue from the external charger to the implanted pulse generator, it is paramount that the charging coil located in or on the implantable pulse generator be spatially arranged relative to the corresponding AC coil of the external charger in a suitable manner. That is, efficient power transmission through the patient's skin from the external charger to the implantable pulse generator via inductive coupling requires constant close alignment between the two devices. Thus, efficiency of the coupling between the external charger and implantable pulse generator is largely dependent upon the alignment between the two coils, and in part, determines what is known as the coupling factor k in a transformer. Achieving a good coupling factor is essential for optimizing efficiency of the inductive link between the external charger and implantable pulse generator. Not only does good coupling increase the power transferred from the external charger to the implantable pulse generator, it minimizes heating in the implantable pulse generator, and also reduces the power requirements of the external charger, which reduces heating of the external charger and minimizes the smaller form factor of the external charger. Proper coupling is also essential for the charging system to function properly, since sufficient coupling is also required for data transfer during the charging process.

To ensure that such constant close alignment between the external charger and implantable pulse generator is achieved, the external charger typically includes an alignment indicator that provides a visual or audible signal that can be used by the patient to reposition or reorient the external charger, thereby maintaining or optimizing the rate at which the implantable pulse generator is charged. However, achieving proper alignment can be difficult due to the lack of differentiation between a deeply implanted pulse generator that is well aligned with the external charger and a shallowly implanted pulse generator that is poorly aligned, i.e., both scenarios appear the same to both the external charger and the implantable pulse generator.

One known approach is to use a charge strength indicator on the external charger to indicate the extent of the charge rate. For example, a bar charge indicator can be used, such that one bar indicates a relatively low charge rate, two bars indicate a greater charge rate, three bars indicate an even greater charge rate, and so forth. One downfall of using a bar charge connection indicator is that the patient must continually looks at the indicator to ensure an optimal charge rate.

Another approach is to use a misalignment indicator on the external charger that signals to the patient with an audible misalignment tone whenever the charge rate falls below the optimal level. However, this approach currently limits the possibility of charging more deeply implanted pulse generators at lower rates without inadvertently triggering the misalignment tone. Although the alignment zone of the external charger could be expanded to prevent such inadvertent triggering of the misalignment tone, the indicator may not generate the misalignment tone when the charge rate actually is less than optimal. Thus, the patient may charge the implantable pulse generator at a sub-optimal rate without ever being warned.

An external charger that combines both a bar charge indicator and a misalignment indicator would still require the patient to monitor the bar charge indicator during charging or endure an audible tone that inappropriately signals for deeper implantable pulse generators. There, thus, remains a need for an improved method and system for indicating alignment or misalignment between an external charger and an implantable pulse generator.

SUMMARY OF THE INVENTION

In accordance with one aspect of the present inventions, a method of controlling the charging of a medical device (e.g., a neurostimulation device) implanted within a patient is provided. The method comprises transcutaneously transmitting electrical energy at a plurality of different frequencies to the implanted medical device. The method further comprises measuring the magnitude of the conveyed electrical energy respectively at the plurality of frequencies. The magnitude of the current within the electrical energy may be measured. For example, if the electrical energy is transcutaneously transmitted from an external charger, the electrical current delivered into a primary coil of the external charger may be measured. The magnitude of electrical energy may be measured at a single relative location or multiple relative locations between the external charger and the implanted medical device.

The method further comprises selecting one of the frequencies based on the measured magnitude of the electrical energy (e.g., the frequency at which the measured magnitude of the electrical energy is the greatest), and setting a charge strength threshold at which a charge strength indicator generates a user-discernible signal based on the selected frequency. In one method, the user-discernible signal is binary signal; for example, an audible signal that indicates the occurrence of a misalignment condition or an alignment condition. In one method, the charge strength threshold is set incrementally higher as the selected frequency incrementally decreases, and is set incrementally lower as the selected frequency incrementally increases. Although the broadest aspects of the present inventions should not be so limited, adjustment of the threshold allows the charge strength indicator to be tailored to the patient and at the particular depth of the implanted medical device, so that the user-discernible signal is generated at the intended times.

One method further comprises determining a depth level at which the medical device is implanted within the patient based on the selected frequency, in which case, the charge strength threshold is set based on the determined depth level. For example, the depth level may be determined to be relatively shallow if the selected frequency is relatively high, and to be relatively deep if the selected frequency is relative low. Determining the depth level may comprise estimating a depth value based on the selected frequency. For example, the depth value may be estimated by comparing the selected frequency to a pre-calibrated frequency/depth curve. The pre-calibrated frequency/depth curve may be stored in a look-up table, in which case, the depth value may be estimated by matching the selected frequency to a frequency value within the look-up table, and obtaining from the look-up table a depth value corresponding to the frequency value.

In accordance with a second aspect of the present invention, an implantable medical system is provided. The medical system comprises an implantable medical device (e.g., a neurostimulation device) and an external charger configured for transcutaneously conveying electrical energy to charge the implanted medical device. The medical system further comprises a charge strength indicator (e.g., an audio transducer) configured for generating a user-discernible signal. In one embodiment, the indicator is a binary indicator, e.g., an alignment indicator or a misalignment indicator.

The medical system further comprises a detector configured for measuring the magnitude of the conveyed electrical energy respectively at the plurality of frequencies, and memory configured for storing a charge strength threshold at which the charge strength indicator generates the user-discernible signal. The medical system further comprises a processor configured for selecting one of the frequencies based on the measured magnitude of the electrical energy, and setting the charge strength threshold based on the selected frequency. The processor can perform these functions in the same manner described above. The detector, charge rate indicator, memory, and processor may be contained within the external charger.

In accordance with a third aspect of the present invention, an external charger for an implantable medical device is provided. The external charger comprises a source of electrical power, and an alternating current (AC) coil configured for transcutaneously conveying electrical energy from the electrical power source to the implanted medical device. The external charger further comprises a charge strength indicator (e.g., an audio transducer) configured for generating a user-discernible signal. In one embodiment, the indicator is a binary indicator, e.g., an alignment indicator or a misalignment indicator.

The external charger further comprises a detector configured for measuring the magnitude of the conveyed electrical energy respectively at the plurality of frequencies, and memory configured for storing a charge strength threshold at which the charge strength indicator generates a user-discernible signal. The external charger further comprises a processor configured for selecting one of the frequencies based on the measured magnitude of the electrical energy, and setting the charge strength threshold based on the selected frequency. The processor can perform these functions in the same manner described above. The external charger may further comprise a portable housing containing the electrical power source, AC coil, charge strength indicator, detector, memory, and processor.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG) or similar electrical stimulator, which may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical and deep brain stimulator, peripheral nerve stimulator, or in any other neural stimulator configured to treat urinary incontinence, sleep apnea, shoulder sublaxation, etc.

Figure 1:
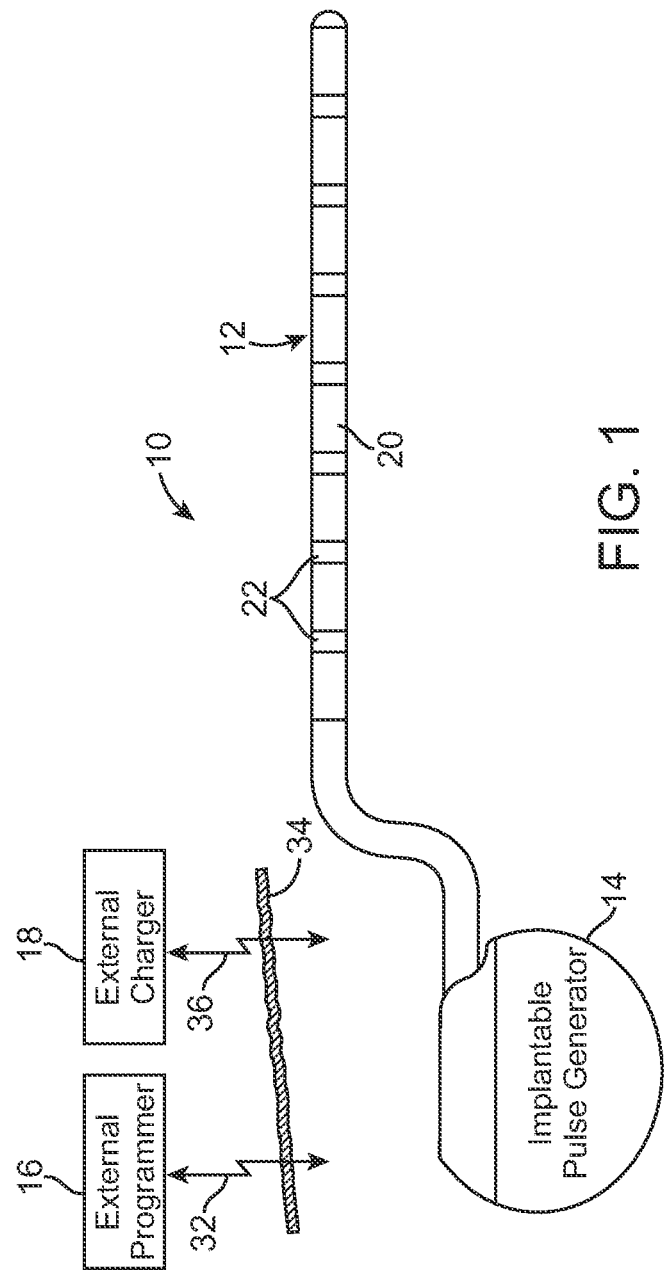
FIG. 1 is plan view of one embodiment of a spinal cord stimulation (SCS) system arranged in accordance with the present inventions.

Turning first to FIG. 1, an exemplary SCS system 10 generally comprises an implantable neurostimulation lead 12, an implantable pulse generator (IPG) 14, an external (non-implanted) programmer 16, and an external (non-implanted) charger 18.

In the illustrated embodiment, the lead 12 is a percutaneous lead and, to that end, includes a plurality of in-line electrodes 20 carried on a flexible body 22. Alternatively, the lead 12 may take the form of a paddle lead. The IPG 14 is electrically coupled to the lead 12 in order to direct electrical stimulation energy to each of the electrodes 20.

The IPG 14 includes an outer case formed from an electrically conductive, biocompatible material, such as titanium and, in some instances, will function as an electrode. The case forms a hermetically sealed compartment wherein the electronic and other components are protected from the body tissue and fluids. For purposes of brevity, the electronic components of the IPG 14, with the exception of the components needed to facilitate the recharging function (described below), will not be described herein. Details of the IPG 14, including the battery, antenna coil, and telemetry and charging circuitry, are disclosed in U.S. Pat. No. 6,516,227, which is expressly incorporated herein by reference.

Figure 2:
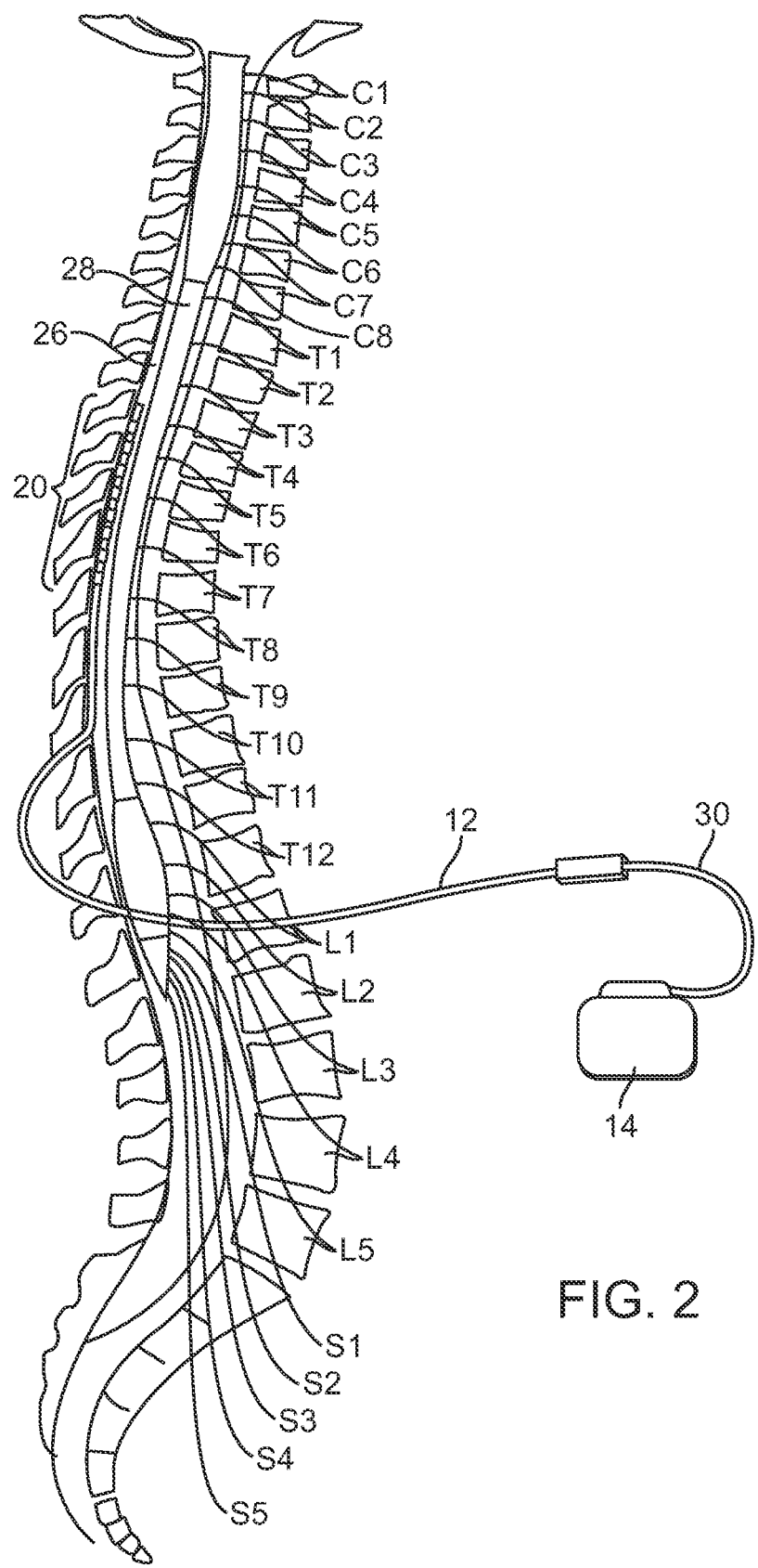
FIG. 2 is a plan view of the SCS system of FIG. 1 in use with a patient.

As shown in FIG. 2, the neurostimulation lead 12 is implanted within the epidural space 26 of a patient through the use of a percutaneous needle or other convention technique, so as to be in close proximity to the spinal cord 28. Once in place, the electrodes 20 may be used to supply stimulation energy to the spinal cord 28 or nerve roots. The preferred placement of the lead 12 is such, that the electrodes 20 are adjacent, i.e., resting upon, the nerve area to be stimulated. Due to the lack of space near the location where the lead 12 exits the epidural space 26, the IPG 14 is generally implanted in a surgically-made pocket either in the abdomen or above the buttocks. The IPG 14 may, of course, also be implanted in other locations of the patient's body. A lead extension 30 may facilitate locating the IPG 14 away from the exit point of the lead 12.

Referring back to FIG. 1, the IPG 14 is programmed, or controlled, through the use of the external programmer 18. The external programmer 18 is transcutaneously coupled to the IPG 14 through a suitable communications link (represented by the arrow 32) that passes through the patient's skin 34. Suitable links include, but are not limited to radio frequency (RF) links, inductive links, optical links, and magnetic links. For purposes of brevity, the electronic components of the external programmer 18 will not be described herein. Details of the external programmer, including the control circuitry, processing circuitry, and telemetry circuitry, are disclosed in U.S. Pat. No. 6,516,227, which has been previously incorporated herein by reference.

The external charger 18 is transcutaneously coupled to the IPG 14 through a suitable link (represented by the arrow 36) that passes through the patient's skin 34, thereby coupling power into the IPG 14 for the purpose of operating the IPG 14 or replenishing a power source, such as a rechargeable battery (e.g., a Lithium Ion battery), within the IPG 14. In the illustrated embodiment, the link 36 is an inductive link; that is, energy from the external charger 18 is coupled to the battery within the IPG 14 via electromagnetic coupling. Once power is induced in the charging coil in the IPG 14, charge control circuitry within the IPG 14 provides the power charging protocol to charge the battery. As will be described in further detail below, the external charger 18 generates an audible tone when misaligned with the IPG 14 to alert the user to adjust the positioning of the external charger 18 relative to the IPG 14. The external charger 18 is designed to charge the battery of the IPG 14 to 80% capacity in two hours, and to 100% in three hours, at implant depths of up to 2.5 cm. When charging is complete, the external charger 18 generates an audible tone to alert the user to decouple the external charger 18 from the IPG 14.

Once the IPG 14 has been programmed, and its power source has been charged or otherwise replenished, the IPG 14 may function as programmed without the external programmer 16 being present. While the external programmer 16 and external charger 18 are described herein as two separate and distinct units, it should be appreciated that the functionality of the external programmer 16 and external charger 18 can be combined into a single unit. It should be noted that rather than an IPG, the SCS system 10 may alternatively utilize an implantable receiver-stimulator (not shown) connected to leads 12, 14. In this case, the power source, e.g., a battery, for powering the implanted receiver, as well as control circuitry to command the receiver-stimulator, will be contained in an external controller/charger inductively coupled to the receiver-stimulator via an electromagnetic link.

Figure 3:
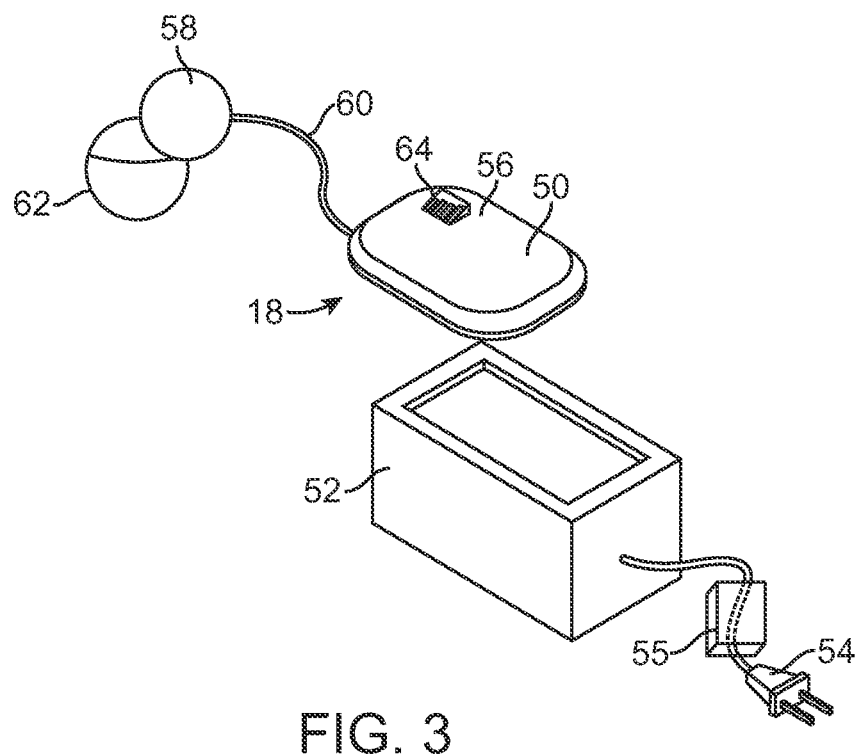
FIG. 3 is a perspective view of one embodiment of an external charger used in the SCS system of FIG. 1.

Referring now to FIG. 3, the external components of the external charger 18 will be described. In this embodiment, the external charger 18 takes the form of a two-part system comprising a portable charger 50 and a charging base station 52. The charging base station 52 includes an AC plug 54, so that it can be easily plugged into any standard 110 volt alternating current (VAC) or 200 VAC outlet. The charging base station 52 further includes an AC/DC transformer 55, which provides a suitable DC voltage (e.g., 5VDC) to the circuitry within the charging base station 52.

The portable charger 50 includes a housing 56 for containing the recharging circuitry, and in particular, the recharging circuitry and battery (not shown in FIG. 3), which will be discussed in further detail below. The housing 56 is shaped and designed in a manner that allows the portable charger 50 to be detachably inserted into the charging base station 52, thereby allowing the portable charger 50, itself, to be recharged. Thus, both the IPG 14 and the portable charger 50 are rechargeable. The portable charger 50 may be returned to the charging base station 52 between uses.

In the illustrated embodiment, the portable charger 50 includes a charging head 58 connected to the housing 56 by way of a suitable flexible cable 60. The charging head 58 houses the AC coil (not shown in FIG. 3) from which the charging energy is transmitted. The portable charger 50 further includes a disposable adhesive pouch 62 or Velcro® strip or patch, which may be placed on the patient's skin over the location where the IPG 14 is implanted. Thus, the charging head 58 may be simply slid into the pouch 62, or fastened to the strip or patch, so that it can be located in proximity to the IPG 14 (e.g., 2-3 cm). In an alternative embodiment, the portable charger 50 does not include a separate charging head, but instead includes a single housing that contains the recharging circuitry, battery, and AC coil.

In order for efficient transfer of energy to the IPG 14, it is important that the charging head 58 (or more particularly, the AC coil within the head 58) be properly aligned with the IPG 14. Thus, in the illustrated embodiment, the portable charger 50 includes a bar charge indicator 64 located on the housing 56, which provides a visual indication of the strength of the charge coupling between the charging head 58 and IPG 14 in the form of bars. As will be described in further detail below, the portable charger 50 comprises a misalignment indicator in the form of an audio transducer that provides an audible indication when the charging head 58 is misaligned relative to the IPG 14. Alternatively, the misalignment indicator can take the form of a vibrating motor. For the purposes of this specification, both the bar charge indicator 64 and misalignment indicator can be considered as charge strength indicators. Once proper alignment with the IPG 14 has been achieved, as indicated by the bar charge indicator 64 or misalignment indicator, the housing 56 may simply be taped in place on the patient's skin using removable medical tape or held in place with a special belt. Typically, charging of the IPG 14 continues until the battery of the IPG 14 has been charged to at least 80% of capacity.

Figure 4:
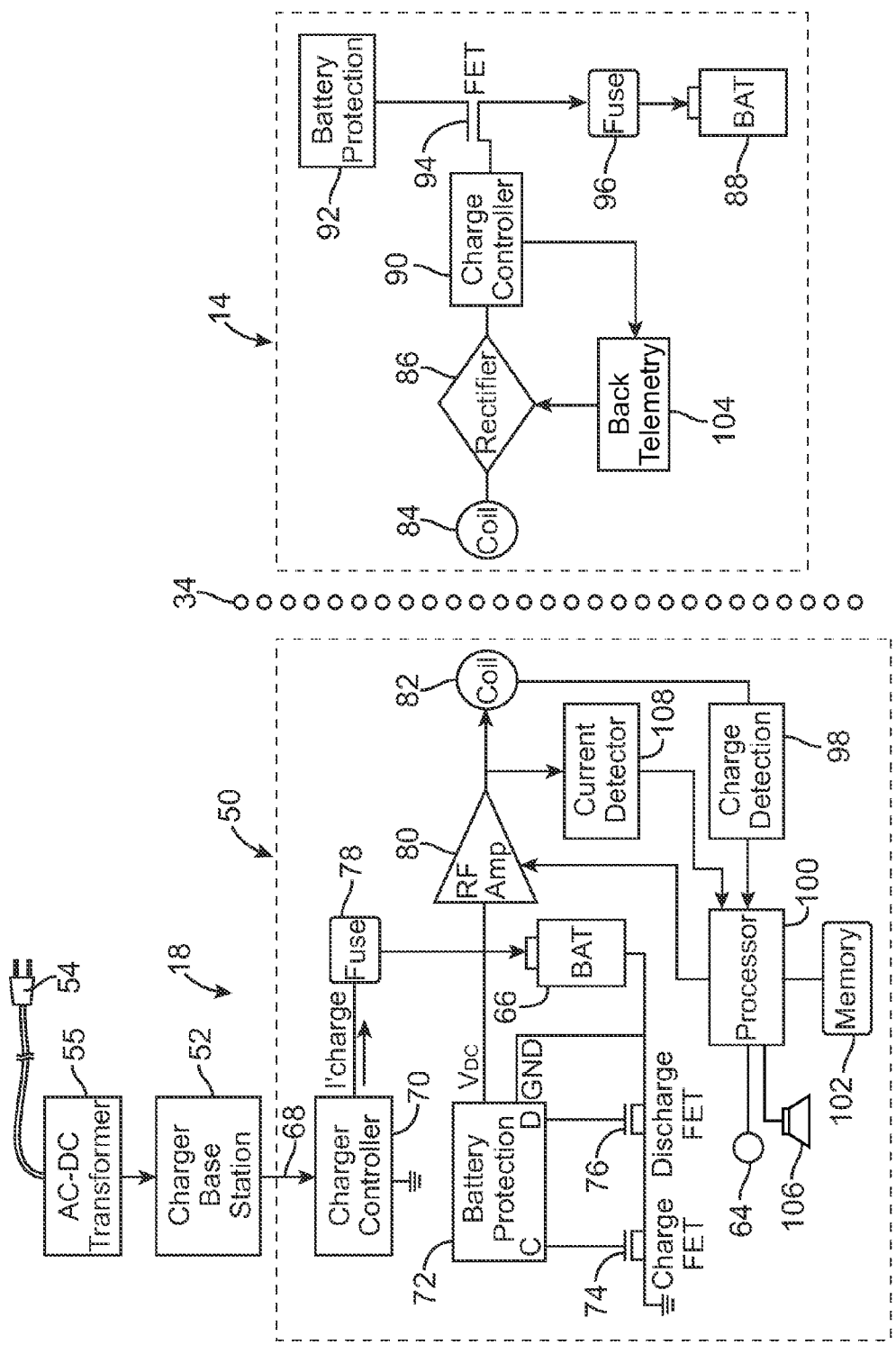
FIG. 4 is a block diagram of the internal components of one embodiment of an external charger and implantable pulse generator used in the SCS system of FIG. 1.

Referring to FIG. 4, the recharging elements of the IPG 14 and portable charger 50 will now be described. It should be noted that the diagram of FIG. 4 is functional only, and is not intended to be limiting. Those of skill in the art, given the descriptions presented herein, should be able to readily fashion numerous types of recharging circuits, or equivalent circuits, that carry out the functions indicated and described.

As previously discussed above, the external charger 18 and IPG 14 are shown inductively coupled together through the patient's skin 34 (shown by dotted line) via the inductive link 36 (shown by wavy arrow). The portable charger 50 includes a battery 66, which in the illustrated embodiment is a rechargeable battery, such as a Lithium Ion battery. Thus, when a recharge is needed, energy (shown by arrow 68) is coupled to the battery 66 via the charging base station 52 in a conventional manner. In the illustrated embodiment, the battery 66 is fully charged in approximately four hours. Once the battery 66 is fully charged, it has enough energy to fully recharge the battery of the IPG 14. If the portable charger 50 is not used and left on charger base station 52, the battery 66 will self-discharge at a rate of about 10% per month. Alternatively, the battery 66 may be a replaceable battery.

The portable charger 50 includes a charge controller 70, which serves to convert the DC power from the AC/DC converter 55 to the proper charge current and voltage for the battery 66, a battery protection circuit 72, which monitors the voltage and current of the battery 66 to ensure safe operation via operation of FET switches 74, 76, and a fuse 78 that disconnects the battery 66 in response to an excessive current condition that occurs over an extended period of time. Further details discussing this control and protection circuitry are described in U.S. Pat. No. 6,516,227, which has been previously incorporated herein by reference.

The portable charger 50 further includes a power amplifier 80, and in particular a radio frequency (RF) amplifier, for converting the DC power from the battery 66 to a large alternating current. The power amplifier may take the form of an E-class amplifier. The portable charger 50 further includes an antenna 82, and in particular a coil, configured for transmitting the alternating current to the IPG 14 via inductive coupling. The coil 82 may comprise a 36 turn, single layer, 30 AWG copper air-core coil having a typical inductance of 45 μH and a DC resistance of about 1.15Ω. The bandwidth the coil 82 is wide enough to accommodate the full range of frequencies at which the coil 82 is operated, and thus, need not be turned for a specific resonance. For purposes that will be described in further detail below, the power amplifier 80 is capable of sweeping the frequency of the current supplied to the 82. For example, the power amplifier 80 may include a voltage-controlled oscillator (VCO) or a Direct Digital Synthesizer (DDS) (not shown) that is capable of varying the frequency of the current output by the power amplifier 80.

The IPG 14 includes an antenna 84, and in particular a coil, configured for receiving the alternating current from the portable charger 50 via the inductive coupling. The coil 84 may be identical to, and preferably has the same resonant frequency as, the coil 82 of the portable charger 50. The IPG 14 further comprises rectifier circuitry 86 for converting the alternating current back to DC power. The rectifier circuitry 86 may, e.g., take the form of a bridge rectifier circuit. The IPG 14 further includes a rechargeable battery 88, such as a Lithium Ion battery, which is charged by the DC power output by the rectifier circuitry 86. In the illustrated embodiment, the battery 88 can be fully charged by the portable charger 50 in under four hours (80% charge in two hours).

The portable charger 50 includes a charge controller 90, which serves to convert the DC power from the rectifier circuitry 86 to the proper charge current and voltage for the battery 88, a battery protection circuit 92, which monitors the voltage and current of the battery 88 to ensure safe operation via operation of a FET switch 94, and a fuse 96 that disconnects the battery 88 in response to an excessive current condition that occurs over an extended period of time. Further details discussing this control and protection circuitry are described in U.S. Pat. No. 6,516,227, which has been previously incorporated herein by reference.

As briefly discussed above, the portable charger 50 is capable of indicating when the battery 88 of the IPG 14 is fully charged or almost fully charged, and when the portable charger 50 is aligned/misaligned with the IPG 14. To this end, the portable charger 50 comprises charge detection circuitry 98 in the form of a passive telemetry data receiver for detecting an electrical parameter indicative of the charge rate of the IPG 14, and a processor 100 for determining the charging qualities of the IPG 14, and in particular, when the IPG 14 is fully charged and when the portable charger 50 is aligned/misaligned with the IPG 14, based on the detected electrical parameter. The charge detection circuitry 98 may comprise separate components for respectively receiving passive data from the IPG 14 and for detecting when the portable charger 50 is aligned/misaligned with the IPG 14. For purposes of brevity, these components are described herein as a single component. The portable charger 50 further comprises memory 102 for storing a charge strength threshold that the processor 100 uses to determine misalignment (or alternatively, alignment) between the portable charger 50 and IPG 14. In the embodiment described below, the charge strength threshold takes the form of a voltage threshold value. The memory 102 also store a computer program used by the processor 100 to perform the functions described below.

In addition to the previously described bar charge indicator 64 (shown in FIG. 3), which visually indicates the charge coupling of the IPG 14 to the user, the portable charger 50 also includes an indicator 106 in the form of an audio transducer (speaker), which signals the user with an audible tone when the battery 88 of the IPG 14 is fully charged and when the portable charger 50 is misaligned with the IPG 14. In alternative embodiments, separate indicators can be used to indicate a full charge state and a misalignment condition.

In the illustrated embodiment, the electrical parameter sensed by the charge detection circuitry 98 is a steady-state voltage having a value V1 at the coil 82, which is indicative of the charge rate of the IPG 14. That is, the voltage value V1 (which is dictated by the reflected impedance from the coil 84 of the IPG 14) is inversely proportional to the coupling between the coils 82, 84 of the respective portable charger 50 and IPG 14, and thus, the charge rate of the IPG 14. Thus, as the reflected impedance and thus the voltage value V1 increases, the charge rate decreases, and as reflected impedance and thus the voltage value V1 decreases, the charge rate increases.

The charge detection circuitry 98 also senses the voltage value V1 at the coil 82 to detect when the IPG 14 has been fully charged. In particular, the IPG 14 includes a back telemetry circuit 104, which detects charge completion of the battery 88 and modulates the secondary load of the IPG 14 by changing the rectifier circuitry 86 from a full-wave rectifier into a half-wave rectifier/voltage clamp. This modulation, in turn, suddenly increases the reflected impedance into the coil 82 of the portable charger 50, which suddenly increases the voltage value V1 (e.g., a transient or pulsed component appears in the detected steady-state voltage) detected by the charge detection circuitry 98.

The processor 100 receives the voltage value V1 from the charge detection circuitry 98, and based on this value, operates the bar charge indicator 64 and audio transducer 106 accordingly. In particular, if the voltage value V1 spikes or suddenly increases, the processor 100 determines that the battery 88 of the IPG 14 is fully charged, and prompts the audio transducer 106 (e.g., by sending a signal) to generate an audible tone or series of audible tones (e.g., an ON-OFF beeping sound), thereby alerting the user that the IPG 14 is fully charged.

The processor 100 operates the bar charge indicator 64 to display the proper number of bars in accordance with the charge rate indicated by the voltage value V1. The processor 100 also compares the voltage value V1 to the electrical parameter threshold value (in this case, a voltage threshold value) stored in the memory 102 to determine misalignment between the portable charger 50 and IPG 14. In particular, the processor 100 compares the voltage value V1 with the voltage threshold value stored in the memory 102 to determine whether a misalignment condition has occurred (i.e., the measured voltage value V1 exceeds the voltage threshold value), and operates the audio transducer 106 in a binary fashion, meaning that it only indicates if a particular condition has been satisfied or not satisfied (i.e., misaligned or not misaligned).

While the modification of a voltage threshold value (or other suitable electrical parameter threshold value) lends itself well to setting the threshold of an audible misalignment tone, thereby ensuring that the patient is alerted only when the portable charger 50 is actually misaligned with the IPG 14, in alternative embodiments, the adjustable voltage threshold value can be used to modify the threshold at which a binary indicator generates a user-discernible signal other than a misalignment signal. For example, the voltage threshold value can correspond to an audio transducer that sounds an alignment tone (i.e., an audible tone that alerts the patient that the portable charger 50 is aligned with the IPG 14), or an indicator that illuminates an alignment light (i.e., a visual signal that alerts the patient that the portable charger 50 is aligned with the IPG 14). In other embodiments, one or more adjustable charge rate threshold values can be used to modify the threshold(s) at which non-binary indicators generate user-discernible signals. For example, the charge rate threshold value(s) can correspond to a bar indicator, such as, e.g., the bar charge indicator 64, such that the thresholds at which the number of bars increases or decreases can be adjusted.

While the illustrated embodiment has been described as performing the charge rate indication and processing functions in the portable charger 50, it should be appreciated that any of these functions can be performed in the charger base station 52, or even the IPG 14. If the indication function is performed by the IPG 14, the user-discernible signal can take the form of a vibration or a modulated electrical stimulation.

Significantly, the voltage threshold value stored in the memory 102 can be varied in order to modify the actual charge rate at which a misalignment condition is deemed to occur. Thus, if the IPG 14 is implanted relatively deep within the patient, the voltage threshold value can be increased, so that the audible misalignment tone does not sound when the charge rate is optimum or otherwise suitable for that implant depth. In contrast, if the IPG 14 is implanted relatively shallow within the patient, the voltage threshold value can be decreased, so that the audible misalignment tone sounds when the charge rate is not optimum or otherwise suitable for that implant depth. Thus, the audible misalignment tone will only sound when the charge rate is sub-optimal for the specific implant depth or orientation. Notably, the charge strength is inversely proportional the voltage value V1, and therefore, it can be said that adjustment of the voltage threshold value is inversely proportional to an adjustment of the charge strength threshold (i.e., an increase in the voltage value threshold is actually a decrease in the charge strength threshold, and a decrease in the voltage value threshold is actually an increase in the charge strength threshold).

Adjustment of the voltage threshold value can be accomplished by automatically determining the depth level at which the IPG 14 is implanted within the patient, with the voltage threshold value being decreased if the depth level is determined to be relatively deep, and the voltage threshold being increased if the depth level is determined to be relatively shallow. Significantly, in determining the depth level of the IPG 14, the processor 100 is capable of sweeping the frequency of the electrical current output from the power amplifier 80 to the coil 82 (e.g., by varying the voltage input to a voltage-controlled oscillator (VCO) within the power amplifier 80). In one embodiment, the processor 100 sweeps the frequency of the electrical current input to the coil 82 in the range from 115 KHz to 77 KHz at 100 Hz intervals.

The relative distance between the IPG 14 and the external charger 50, and thus, the depth level of the IPG 14 within the patient, can be determined by measuring the magnitude of the electrical current input into the coil 80 at the respective different frequencies, and determining the depth level based on the measured electrical current magnitudes. Other electrical parameters, e.g., the steady-state voltage value V1, can be measured to determine the depth level of the IPG 14. Such measurements can be performed in the external charger 50 or the IPG 14. Notably, if the IPG 14 is relatively far away from the external charger 50 (i.e., the depth level of the IPG 14 is relatively deep), the measured electrical current will peak at a relatively low frequency, and if the IPG 14 is relatively close to the external charger 50 (i.e., the depth level of the IPG 14 is relatively shallow), the measured electrical current will peak at a relatively high frequency. Thus, the depth level of the IPG 14 may be determined by identifying the frequency at which the measured electrical current is the greatest.

To this end, the external charger 50 comprises an electrical current detector 108 that measures the magnitude of the electrical current input from the power amplifier 80 into the coil 82, and continually outputs the measured magnitudes to the processor 100 as the frequency of the current is varied. The processor 100 identifies the frequency at which the measured electrical current is the greatest, stores this frequency within memory 102, and based on this frequency, determines the depth level of the IPG 14 (i.e., determines the depth level to be relatively shallow if the determined frequency is relatively high, and determines the depth level to be relatively deep if the determined frequency is relatively low). In some cases, if the external charger 50 is moved around during the monitoring process, different frequencies at which the measured electrical current is the greatest will occur, in which case, the processor 100 will store the highest frequency at which the measured electrical current is the greatest, and use that to determine the depth level of the IPG 14. Based on the determined depth level, the processor 100 will automatically modify the voltage threshold value stored in the memory 102, with the voltage threshold value being set to a relatively high value if the depth level of the IPG 14 is determined to be relatively deep, and the voltage threshold value being set to a relatively low value if the depth level of the IPG 14 is relatively shallow.

Figures 5, 6:
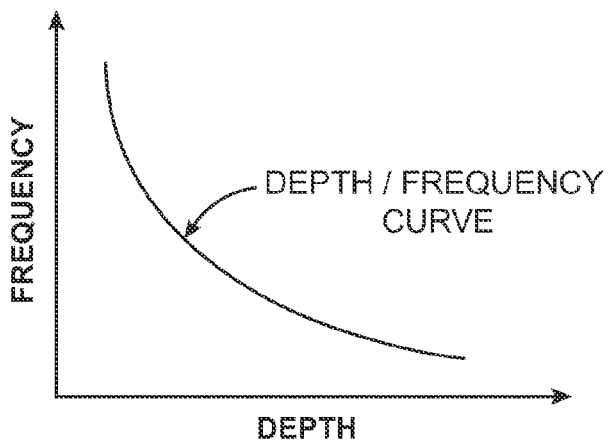
FIG. 5 is an exemplary plot of a frequency/depth curve used by the external charger to determine the depth of an implantable pulse generator within a patient.
FIG. 6 is a frequency/depth look-up table that can be used to store the frequency/depth curve of FIG. 5.

In one embodiment, the processor 100 is configured for estimating the depth level of the IPG 14 by comparing the frequency at which the greatest magnitude of the electrical current was measured to a pre-calibrated curve of frequencies versus depth, an exemplary one of which is illustrated in FIG. 5. The pre-calibrated frequency/depth curve can be generated using a variety of means, such as implanting an IPG at various known sample depths in tissue and measuring the current input into the coil of an external charger while sweeping the frequency range for each implant depth. Additional data points may optionally be added to the pre-calibrated frequency curve depth to increase the depth estimation by interpolating between the measured data points.

The pre-calibrated frequency/depth curve may be stored in the memory 102 as a look-up table, as illustrated in FIG. 6. In this case, the processor 100 may recall the look-up table and compare the frequency value at which the greatest magnitude of the electrical current was measured to the frequencies values contained within the look-up table. The depth of the IPG 14 can then be estimated as the depth value corresponding to the stored frequency value that best matches the measured frequency value. For example, if the frequency value at which the greatest magnitude of the electrical current was measured is 114.5 KHz, the depth of the IPG 16 will be estimated to be 49.375 mm.

The processor 100 can then adjust the voltage threshold value stored in memory 102 to a value corresponding to the estimated depth value, with the voltage threshold value incrementally increasing as the estimated depth value incrementally increases, and the voltage threshold value incrementally decreasing as the estimated depth value incrementally decreases. Alternatively, the depth values stored in the look-up table can be replaced with corresponding voltage threshold values, so that the processor 100 can directly obtain the voltage threshold value from the look-up table without estimating the depth value.

Notably, the resolution of the look-up table, and thus the accuracy of the estimated depth, will depend on the intervals of the frequency range at which the electrical current magnitude is measured. For example, in the exemplary case wherein the frequency of the electrical current is swept in the range from 115 KHz to 77 KHz at 100 Hz intervals, the look-up table will have 381 magnitude values and 381 corresponding frequency values, and therefore, the number of depth values, and thus voltage threshold values, from which the processor 100 may select is 381.

Figure 7:
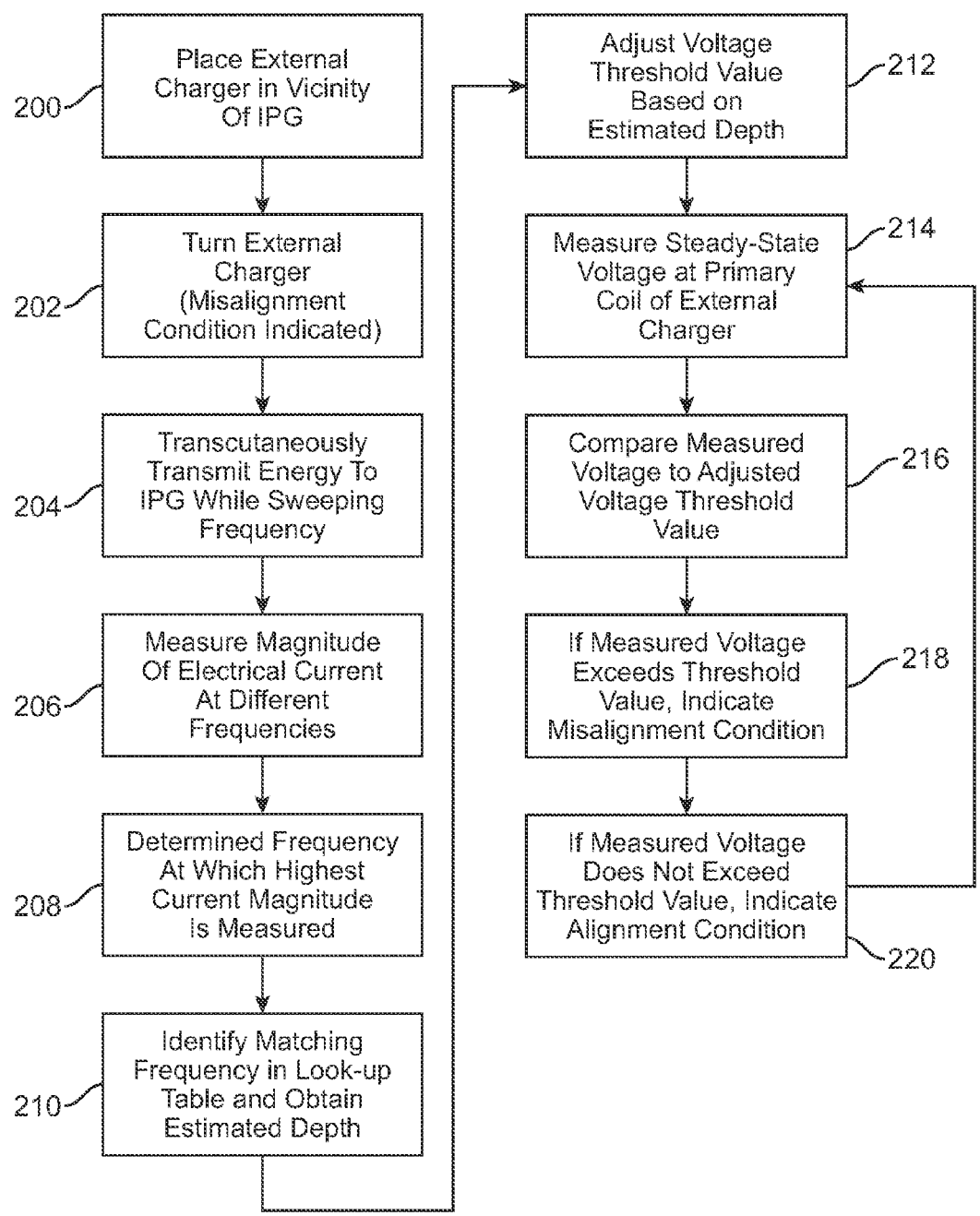
FIG. 7 is a flow diagram of a method used by the external charger to charge the implantable pulse generator.

Having described the structure and function of the charging system, one method of recharging the IPG 14 with the external charger 50 will now be described with reference to FIG. 7. First, the external charger 50 is placed in the general vicinity of the implanted IPG 14 (step 200). Then, the external charger 50 is turned on, at which time it will generate an audible misalignment tone to indicate a misalignment condition until the external charger 50 is sufficiently aligned with the IPG 14 (step 202). Alternatively, the external charger 50 will generate an audible alignment tone to indicate an alignment condition only when the external charger 50 is sufficiently aligned with the IPG 14. The external charger 50 will then begin transcutaneously transmitting electrical energy to charge the implanted IPG, while sweeping the frequency of the electrical current provided to the primary coil 82 of the external charger 50 (step 204). While the frequency of the electrical current is swept, the magnitude of the electrical current is measured at the different frequencies (step 206).

The external charger 50 may either be maintained at the same relative location to the IPG 14 at the site, in which case, a single set of electrical current magnitudes will be obtained for the entire frequency range, or the external charger 50 may be slowly moved around at the site, in which case, multiple sets of electrical current magnitudes will be obtained for the entire frequency range to in order to map the site. In either case, external charger 50 determines the frequency at which the magnitude of the electrical current peaks and stores the highest frequency (step 208). The external charger 50 then estimates the depth of the IPG 14 by accessing the frequency/depth look-up table stored in memory 102, identifying within the look-up table the frequency value that matches the determined highest frequency, and selecting the corresponding depth value from the look-up table (step 210). Next, voltage threshold value stored in memory 102 is set or adjusted to a value based on the estimated depth of the IPG 14; with the adjusted voltage threshold value being incrementally higher as the estimated depth decreases, and the adjusted voltage threshold value being incrementally lower as the estimated depth increases (step 212).

After adjustment of the voltage threshold value, the stead steady-state voltage value V1 at the coil 102 is measured (step 214) and compared to the voltage threshold value (step 216). If the voltage value V1 exceeds the voltage threshold value, the audible sound will continue to indicate the continued presence of the misalignment condition (step 218), and if the voltage value V1 does not exceed the voltage threshold value, the audible sound will be stopped to indicate an alignment condition (step 220). Alternatively, if the voltage value V1 exceeds the voltage threshold value, no audible sound will be generated to indicate the continued presence of the misalignment condition, and if the voltage value V1 does not exceed the voltage threshold value, the audible sound will be generated to indicate an alignment condition. Steps 214-220 can then be repeated without adjusting the voltage threshold value. The process can return to step 204 to readjust the voltage threshold value.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of controlling the charging of a medical device implanted within a patient, comprising:
   transcutaneously transmitting electrical energy at a plurality of different frequencies to the implanted medical device;
   measuring the magnitude of the transmitted electrical energy respectively at the plurality of frequencies;
   selecting one of the frequencies based on the measured magnitude of the electrical energy;
   consulting data correlating frequencies with charge strength threshold values to select a charge strength threshold using the selected frequency; and
   setting a charge strength threshold at which a charge strength indicator generates a user-discernible signal to the selected charge strength threshold.

2. The method of claim 1, wherein the selected frequency is the frequency at which the measured magnitude of the electrical energy is the greatest.

3. The method of claim 1, wherein the charge strength threshold is set incrementally higher as the selected frequency incrementally decreases, and the charge strength threshold is set incrementally lower as the selected frequency incrementally increases.

4. The method of claim 1, wherein the data further correlates frequencies with depth levels at which the medical device is implanted, and wherein the data is consulted to select a depth using the selected frequency, and the selected depth is used to select the charge strength threshold.

5. The method of claim 4, wherein the selected depth is determined to be relatively shallow if the selected frequency is relatively high, and the selected depth is determined to be relatively deep if the selected frequency is relative low.

6. The method of claim 4, wherein selecting the depth comprises estimating a depth value based on the selected frequency using the data.

7. The method of claim 6, wherein the depth value is estimated by comparing the selected frequency to a pre-calibrated frequency/depth curve in the data.

8. The method of claim 1, wherein measuring the magnitude of the electrical energy comprises measuring the magnitude of a current within the electrical energy.

9. The method of claim 8, wherein the electrical energy is transcutaneously transmitted from an external charger, and the current within the electrical energy is the electrical current delivered into a primary coil of the external charger.

10. The method of claim 1, wherein the electrical energy is transcutaneously transmitted from an external charger, and the magnitude of electrical energy is measured at a single relative location between the external charger and the implanted medical device.

11. The method of claim 1, wherein the electrical energy is transcutaneously transmitted from an external charger, and the magnitude of electrical energy is measured at multiple relative locations between the external charger and the implanted medical device.

12. An implantable medical system, comprising:
   an implantable medical device;
   an external charger configured for transcutaneously transmitting electrical energy at a plurality of different frequencies to the implanted medical device;
   a charge strength indicator configured for generating a user-discernible signal;
   a detector configured for measuring the magnitude of the transmitted electrical energy respectively at the plurality of frequencies;
   memory configured for storing a charge strength threshold at which the charge strength indicator generates the user-discernible signal; and
   a processor configured to select one of the frequencies based on the measured magnitude of the electrical energy,
      consult stored data correlating frequencies with charge strength threshold values to select the charge strength threshold using the selected frequency, and
      store the selected charge strength threshold in the memory.

13. The system of claim 12, wherein the selected frequency is the frequency at which the measured magnitude of the electrical energy is the greatest.

14. The system of claim 12, wherein the processor is configured to store incrementally higher values for the selected charge strength threshold as the selected frequency incrementally decreases, and store incrementally lower values for the selected charge strength threshold as the selected frequency incrementally increases.

15. The system of claim 12, wherein the processor is further configured to determine a depth at which the medical device is implanted within a patient based on the selected frequency, and to select the charge strength threshold based on the determined depth.

16. The system of claim 15, wherein the processor is configured to determine the depth to be relatively shallow if the selected frequency is relatively high, and relatively deep if the selected frequency is relative low.

17. The system of claim 15, wherein the processor is configured to determine the depth by estimating a depth value based on the selected frequency by consulting stored data correlating frequencies with depth values.

18. The system of claim 17, wherein the data correlating frequencies with depth values is stored in the memory.

19. The system of claim 12, wherein the data correlating frequencies with charge strength threshold values is stored in the memory.

20. The system of claim 12, wherein the detector is configured for measuring the magnitude of the electrical energy by measuring the magnitude of a current within the electrical energy.

21. The system of claim 20, wherein the current within the electrical energy is the electrical current delivered into a primary coil of the external charger.

22. The system of claim 12, wherein the charge strength indicator, detector, memory, and processor are contained within the external charger.

23. An external charger for an implantable medical device, comprising:

a source of electrical power;

an alternating current (AC) coil configured for transcutaneously transmitting electrical energy at a plurality of different frequencies from the electrical power source to the implanted medical device;

a charge strength indicator configured for generating a user-discernible signal;

a detector configured for measuring the magnitude of the transmitted electrical energy respectively at the plurality of frequencies;

memory configured for storing a charge strength threshold at which the charge strength indicator generates a user-discernible signal; and a processor configured to
- select one of the frequencies based on the measured magnitude of the electrical energy,
- consult stored data correlating frequencies with charge strength threshold values to select the charge strength threshold using the selected frequency, and
- store the selected charge strength threshold in the memory.

24. The external charger of claim 23, wherein the selected frequency is the frequency at which the measured magnitude of the electrical energy is the greatest.

25. The external charger of claim 23, wherein the processor is configured to store incrementally higher values for the selected charge strength threshold as the selected frequency incrementally decreases, and store incrementally lower values for the selected charge strength threshold as the selected frequency incrementally increases.

26. The external charger of claim 23, wherein the processor is further configured to determine a depth at which the medical device is implanted within a patient based on the selected frequency, and to select charge strength threshold based on the determined depth.

27. The external charger of claim 26, wherein the processor is configured to determine the depth to be relatively shallow if the selected frequency is relatively high, and relatively deep if the selected frequency is relative low.

28. The external charger of claim 26, wherein the processor is configured to determine the depth by estimating a depth value based on the selected frequency by consulting stored data correlating frequencies with depth values.

29. The external charger of claim 28, wherein the data correlating frequencies with depth values is stored in the memory.

30. The external charger of claim 23, wherein the data correlating frequencies with charge strength threshold values is stored in the memory.

31. The external charger of claim 23, wherein the detector is configured for measuring the magnitude of the electrical energy by measuring the magnitude of a current within the electrical energy.

32. The external charger of claim 31, wherein the current within the electrical energy is the electrical current delivered into the AC coil.

33. The external charger of claim 23, further comprising a portable housing containing the electrical power source, AC coil, charge strength indicator, detector, memory, and processor.

* * * * *